United States Patent [19]

Elbe et al.

[11] Patent Number: 5,371,065
[45] Date of Patent: Dec. 6, 1994

[54] SUBSTITUTED AZOLYLMETHYLOXIRANES

[75] Inventors: Hans-Ludwig Elbe, Wuppertal; Karl H. Büchel, Burscheid; Wilhelm Brandes, Leichlingen; Stefan Dutzmann, Duesseldorf; Klaus Lürssen, Bergisch-Gladbach, all of Germany

[73] Assignee: Bayer Aktiengesellschaft, Leverkusen, Germany

[21] Appl. No.: 305,836

[22] Filed: Feb. 2, 1989

[30] Foreign Application Priority Data

Feb. 9, 1988 [DE] Germany .................. 3803833

[51] Int. Cl.$^5$ .................. A01N 43/653; C07D 249/08
[52] U.S. Cl. .................. 504/272; 514/184; 514/383; 548/101; 548/268.8
[58] Field of Search .................. 71/92, 76; 514/184, 514/383; 548/101, 262, 268.8; 504/272

[56] References Cited

U.S. PATENT DOCUMENTS

| 4,416,682 | 11/1983 | Worthington | 71/92 |
| 4,464,381 | 8/1984 | Janssen et al. | 514/383 |
| 4,499,281 | 2/1985 | Holmwood et al. | 71/92 |

FOREIGN PATENT DOCUMENTS

| 6700586 | 4/1987 | Australia | 548/262 |
| 0061835 | 10/1982 | European Pat. Off. . | |
| 0131845 | 1/1985 | European Pat. Off. . | |
| 3245504 | 6/1984 | Germany . | |
| 3307218 | 9/1984 | Germany . | |

OTHER PUBLICATIONS

Journal of Heterocyclic Chemistry, vol. 25, pp. 1439–1441 (1988).

*Primary Examiner*—Patricia L. Morris
*Attorney, Agent, or Firm*—Sprung, Horn, Kramer & Woods

[57] ABSTRACT

Fungicidal and plant growth-regulating substituted azolylmethyloxiranes of the formula

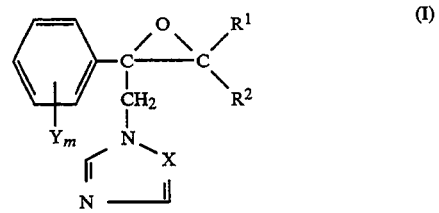

in which
  $R^1$ stands for alkyl,
  $R^2$ stands for alkyl,
  X stands for a nitrogen atom or the CH group,
  Y stands (or halogen, alkyl, cycloalkyl, alkoxy, alkylthio, halogenoalkyl, halogenoalkoxy, halogenoalkylthio, optionally substituted phenyl, optionally substituted phenoxy, optionally substituted phenylalkyl and/or optionally substituted phenylalkoxy and
  m stands for the numbers 0, 1, 2 or 3, and addition products thereof with acids and metal salts.

11 Claims, No Drawings

SUBSTITUTED AZOLYLMETHYLOXIRANES

The present invention relates to new substituted azolylmethyloxiranes, a process for their preparation and their use as fungicides and plant growth regulators.

It has already been disclosed that certain hydroxyalkylazoles exhibit fungicidal properties (cf. DE-OS (German Published Specification) 3,245,504). Thus, for example 3-(4-chloro-phenylthio)-2-(4-chlorophenyl)-3,3-dimethyl-1-(imidazol-1-yl)-2-propanol, 3-(2,4-dichloro-phenoxy)-2-(4-chlorophenyl)-3,3-dimethyl-1-(imidazol-1-yl )-2-propanol and 2-(4-chlorophenyl)-4-(4-fluorophenyl)-3,3-dimethyl-1-(1,2,4-triazol-1-yl)-2-butanol can be employed for combating fungi. However, the activity of these substances is not always completely satisfactory, in particular at low application rates and when low concentrations are used.

New substituted azolylmethyloxiranes of the formula

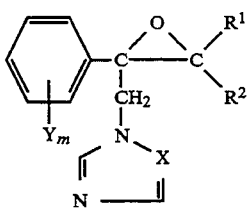

in which
R$^1$ stands for alkyl,
R$^2$ stands for alkyl,
X stands for a nitrogen atom or the CH group,
Y stands for halogen, alkyl, cycloalkyl, alkoxy, alkylthio, halogenoalkyl, halogenoalkoxy, halogenoalkylthio, optionally substituted phenyl, optionally substituted phenoxy, optionally substituted phenylalkyl and/or optionally substituted phenylalkoxy and
m stands for the numbers 0, 1, 2 or 3,
and their acid addition salts and metal salt complexes have now been found.

In the event that R$^1$ and R$^2$ are different from one another, the new substituted azolylmethyloxiranes of the formula (I) possess two adjacent carbon atoms which are asymmetrically substituted. Therefore, they can be present in the two geometrical isomers (threo and erythro form) which can be obtained in various quantitative ratios. The invention relates both to the individual isomers and to their mixtures.

Furthermore, it has been found that substituted azolylmethyloxiranes of the formula (I) or their acid addition salts and metal salt complexes are obtained when hydroxyalkylazoles of the formula

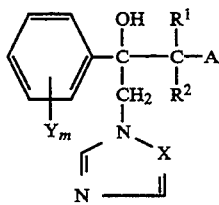

in which

R$^1$, R$^2$, X, Y and m have the abovementioned meaning and
A stands for a nucleophilic leaving group,
are reacted with strong bases, if appropriate in the presence of a diluent, and the resulting compounds of the formula (I) are then, if appropriate, subjected to an addition reaction with an acid or a metal salt.

Finally, it has been found that the new substituted azolylmethyloxiranes of the formula (I) and their acid addition salts and metal salt complexes possess very good fungicidal and plant growth-regulating properties.

Surprisingly, the substances according to the invention are distinguished by a better fungicidal action than similar compounds which are known from the prior art and which are used in the same field of application. Thus, the substances according to the invention are superior to, for example, 3-(4-chloro-phenylthio)-2-(4-chloro-phenyl)-3,3-dimethyl-1-(imidazol-1-yl)-2-propanol, 3-(2,4-dichloro-phenoxy)-2-(4-chlorophenyl)-3,3-dimethyl-1-(imidazol-1-yl)-2-propanol and 2-(4-chlorophenyl)-4-(4-fluorophenyl)-3,3-dimethyl -1-(1,2,4-triazol-1-yl)-2-butanol, with reference to their fungicidal properties.

In addition, the new substituted azolylmethyloxiranes of the formula (I) are interesting intermediates for the preparation of further active compounds for plant protection. Thus, fungicides and antimycotic agents can be obtained by appropriate reactions of the oxiranes with triazoles or imidazoles (EP-OS (European Published Specification) 0,131,845 and DE-OS (German Published Specification) 3,307,218). Furthermore, known fungicides can be obtained by reacting the oxiranes with an oxygen- or sulphur-nucleophile (cf. EP-OS (European Published Specification) 0,061,835).

Formula (I) provides a general definition of the substituted azolylmethyloxiranes according to the invention. Preferred compounds of the formula (I) are those in which
R$^1$ stands for straight-chain or branched alkyl having 1 to 4 carbon atoms,
R$^2$ stands for straight-chain branched alkyl having 1 to 4 carbon atoms,
X stands for a nitrogen atom or the CH group,
Y stands for halogen, alkyl having 1 to 4 carbon atoms, cycloalkyl having 3 to 7 carbon atoms, alkoxy having 1 to 4 carbon atoms, alkylthio having 1 to 4 carbon atoms, halogenoalkyl having 1 or 2 carbon atoms and 1 to 5 identical or different halogen atoms, in particular fluorine and/or chlorine atoms, halogenoalkoxy having 1 or 2 carbon atoms and 1 to 5 identical or different halogen atoms, in particular fluorine and/or chlorine atoms, halogenoalkylthio having 1 or 2 carbon atoms and 1 to 5 identical or different halogen atoms, in particular fluorine and/or chlorine atoms, and also stands for phenyl which is optionally substituted by halogen and/or alkyl having 1 or 2 carbon atoms, for phenoxy which is optionally substituted by halogen and/or alkyl having 1 or 2 carbon atoms, for phenylalkyl which has 1 or 2 carbon atoms in the alkyl moiety and which is optionally substituted by halogen and/or alkyl having 1 or 2 carbon atoms and/or for phenylalkoxy which has 1 or 2 carbon atoms in the alkoxy moiety and which is optionally substituted by halogen and/or alkyl having 1 or 2 carbon atoms, and
m stands for the numbers 0, 1, 2 or 3.

If m stands for the numbers 2 or 3, the meanings of Y can be identical or different.

Particularly preferred compounds of the formula (I) are those in which
  R stands for methyl or ethyl,
  R stands for methyl or ethyl,
  X stands for a nitrogen atom or the CH group,
  Y stands for fluorine, chlorine, bromine, methyl, isopropyl, t-butyl, cyclohexyl, methoxy, methylthio, trifluoromethyl, trifluoromethoxy, trifluoromethylthio, and also stands for phenyl which is optionally substituted by fluorine, chlorine and/or methyl, for phenoxy which is optionally substituted by fluorine, chlorine and/or methyl, for benzyl which is optionally substituted by fluorine, chlorine and/or methyl, and/or for benzyloxy which is optionally substituted by fluorine, chlorine and/or methyl, and
  m stands for the numbers 0, 1, 2 or 3.

Other preferred compounds according to the invention are addition products of acids and those substituted azolylmethyloxiranes of the formula (I) in which the substituents $R^1$, $R^2$, X, Y and the index m have the meanings which have already been preferably mentioned for these substituents and this index.

The acids which can be subjected to the addition reaction preferably include hydrohalic acids, such as, for example, hydrochloric acid and hydrobromic acid, in particular hydrochloric acid, furthermore phosphoric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as p-toluenesulphonic acid and 1,5-naphthalenedisulphonic acid, and also saccharin and thiosaccharin.

Other preferred compounds according to the invention are addition products of salts of metals of main groups II to IV and of subgroups I and II and also IV to VIII of the Periodic Table of the Elements and those substituted azolytmethyloxiranes of the formula (I) in which the substituents $R^1$, $R^2$, X and Y and the index m have the meanings which have already been preferably mentioned for these substituents and this index.

Salts which are particularly preferred in this reaction are those of copper, zinc, manganese, magnesium, tin, iron and of nickel. Suitable anions of these salts are those which are derived from those acids which give physiologically tolerable addition products. Acids of this type which are particularly preferred in this context are the hydrohalic acids, such as, for example, hydrochloric acid and hydrobromic acid, and nitric acid and sulphuric acid.

Examples, which may be mentioned, of particularly preferred compounds of the formula (I) according to the invention the azolylmethyloxiranes compiled Table 1 below.

TABLE 1

| $Y_m$ | $R^1$ | $R^2$ | X |
|---|---|---|---|
| 2,4-F$_2$ | CH$_3$ | CH$_3$ | N (CH) |
| 2-F, 4-CF$_3$ | CH$_3$ | CH$_3$ | " |
| 2-F, 4-OCF$_3$ | CH$_3$ | CH$_3$ | " |
| 2-F, 4-SCF$_3$ | CH$_3$ | CH$_3$ | " |
| 4-OCF$_3$ | CH$_3$ | CH$_3$ | " |
| 4-SCF$_3$ | CH$_3$ | CH$_3$ | " |
| 4-F | CH$_3$ | CH$_3$ | " |
| 3-F | CH$_3$ | CH$_3$ | " |
| 2-F | CH$_3$ | CH$_3$ | " |
| 2-Cl, 4-F | CH$_3$ | CH$_3$ | " |
| 2-F, 4-Cl | CH$_3$ | CH$_3$ | " |
| 3-Cl, 4-OCF$_3$ | CH$_3$ | CH$_3$ | " |
| 3-Cl, 4-SCF$_3$ | CH$_3$ | CH$_3$ | " |
| 3,4-Cl$_2$ | CH$_3$ | CH$_3$ | N (CH) |
| 2,4-Cl$_2$ | CH$_3$ | CH$_3$ | " |
| 3,4,6-Cl$_3$ | CH$_3$ | CH$_3$ | " |
| 3,4,6-F$_3$ | CH$_3$ | CH$_3$ | " |
| 3-F, 4,6-Cl$_2$ | CH$_3$ | CH$_3$ | " |
| 4-Br | CH$_3$ | CH$_3$ | " |
| 2-Br | CH$_3$ | CH$_3$ | " |
| 4-OCH$_3$ | CH$_3$ | CH$_3$ | " |
| 4-phenyl | CH$_3$ | CH$_3$ | " |
| 4-O-(4-Cl-phenyl) | CH$_3$ | CH$_3$ | " |
| 4-CH$_3$ | CH$_3$ | CH$_3$ | " |
| 4-(4-Cl-phenyl) | CH$_3$ | CH$_3$ | " |
| 4-cyclohexyl | CH$_3$ | CH$_3$ | " |
| 4-SCH$_3$ | CH$_3$ | CH$_3$ | " |
| 4-OCHF$_2$ | CH$_3$ | CH$_3$ | " |
| 4-OCF$_2$Cl | CH$_3$ | CH$_3$ | " |
| 3-Cl, 4-OCHF$_2$ | CH$_3$ | CH$_3$ | " |
| 3-Cl, 4-OCF$_2$Cl | CH$_3$ | CH$_3$ | " |
| 4-SCHF$_2$ | CH$_3$ | CH$_3$ | " |
| 2,4-F$_2$ | CH$_3$ | C$_2$H$_5$ | N (CH) |
| 2-F, 4-CF$_3$ | CH$_3$ | C$_2$H$_5$ | " |
| 2-F, 4-OCF$_3$ | CH$_3$ | C$_2$H$_5$ | " |
| 2-F, 4-SCF$_3$ | CH$_3$ | C$_2$H$_5$ | " |
| 4-OCF$_3$ | CH$_3$ | C$_2$H$_5$ | " |
| 4-SCF$_3$ | CH$_3$ | C$_2$H$_5$ | " |
| 4-F | CH$_3$ | C$_2$H$_5$ | " |
| 3-F | CH$_3$ | C$_2$H$_5$ | " |
| 2-F | CH$_3$ | C$_2$H$_5$ | " |
| 2-Cl, 4-F | CH$_3$ | C$_2$H$_5$ | " |
| 2-F, 4-Cl | CH$_3$ | C$_2$H$_5$ | " |
| 3-Cl, 4-OCF$_3$ | CH$_3$ | C$_2$H$_5$ | " |
| 3-Cl, 4-SCF$_3$ | CH$_3$ | C$_2$H$_5$ | " |
| 3,4-Cl$_2$ | CH$_3$ | C$_2$H$_5$ | " |
| 2,4-Cl$_2$ | CH$_3$ | C$_2$H$_5$ | " |
| 3,4,6-Cl$_3$ | CH$_3$ | C$_2$H$_5$ | " |

TABLE 1-continued (I)

| $Y_m$ | $R^1$ | $R^2$ | X |
|---|---|---|---|
| 3,4,6-F$_3$ | CH$_3$ | C$_2$H$_5$ | " |
| 3-F, 4,6-Cl$_2$ | CH$_3$ | C$_2$H$_5$ | " |
| 4-Br | CH$_3$ | C$_2$H$_5$ | " |
| 2-Br | CH$_3$ | C$_2$H$_5$ | " |
| 4-OCH$_3$ | CH$_3$ | C$_2$H$_5$ | " |
| 4—⟨phenyl⟩ | CH$_3$ | C$_2$H$_5$ | N (CH) |
| 4—O—⟨C$_6$H$_4$⟩—Cl | CH$_3$ | C$_2$H$_5$ | " |
| 4-CH$_3$ | CH$_3$ | C$_2$H$_5$ | " |
| 4—⟨C$_6$H$_4$⟩—Cl | CH$_3$ | C$_2$H$_5$ | " |
| 4—⟨C$_6$H$_{10}$⟩—H | CH$_3$ | C$_2$H$_5$ | " |
| 4-SCH$_3$ | CH$_3$ | C$_2$H$_5$ | " |
| 4-OCHF$_2$ | CH$_3$ | C$_2$H$_5$ | " |
| 4-OCF$_2$Cl | CH$_3$ | C$_2$H$_5$ | " |
| 3-Cl, 4-OCHF$_2$ | CH$_3$ | C$_2$H$_5$ | " |
| 3-Cl, 4-OCF$_2$Cl | CH$_3$ | C$_2$H$_5$ | " |
| 4-SCHF$_2$ | CH$_3$ | C$_2$H$_5$ | " |
| 4-Cl | CH$_3$ | C$_2$H$_5$ | " |
| 3-Cl | CH$_3$ | C$_2$H$_5$ | " |
| 2-Cl | CH$_3$ | C$_2$H$_5$ | " |
| 4-Cl | C$_2$H$_5$ | C$_2$H$_5$ | " |
| 3-Cl | C$_2$H$_5$ | C$_2$H$_5$ | " |
| 2-Cl | C$_2$H$_5$ | C$_2$H$_5$ | " |

If, for example, 3,3-dimethyl-3-phenoxy-2-phenyl-1-(1,2,4-triazol-1-yl)-2-propanol is used as the starting substance, sodium hydride is used as the base and dioxane is used as the solvent, the course of the process according to the invention may be represented by the following equation:

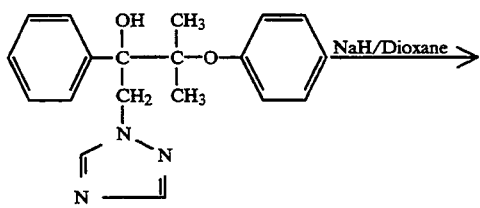

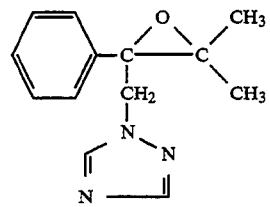

Formula (II) provides a general definition of the hydroxyalkylazoles required as starting substances when carrying out the process according to the invention. In this formula, $R^1$, $R^2$, X, Y and m preferably have those meanings which have already been preferably mentioned for these radicals and this index in connection with the description of the substances of the formula (I) according to the invention.

A preferably stands for a phenolate, 4-chlorophenolate or thiophenolate radical.

The hydroxyalkylazoles of the formula (II) are known or can be prepared by processes which are known from the literature (cf. DE-OS (German Published Specification) 3,245,504).

Diluents which can be employed for carrying out the process according to the invention are all customary inert organic solvents. Solvents which can preferably be used are ethers, such as tetrahydrofuran and dioxane; aromatic hydrocarbons, such as toluene and xylene, and aliphatic and cycloaliphatic hydrocarbons, such as hexane and cyclohexane.

Bases which can be employed for carrying out the process according to the invention are all strong bases which can customarily be used for reactions of this type. Preferably suitable bases are alkali metal hydroxides, such as, for example, sodium hydroxide and potassium hydroxide, alkali metal alkoxides, such as, for example, sodium methoxide, sodium ethoxide, sodium n-propoxide, sodium t-butoxide, potassium methoxide, potassium ethoxide, potassium n-propoxide and potassium t-butoxide, and also hydrides, such as, for example, sodium hydride.

When carrying out the process according to the invention, the reaction temperatures can be varied within a relatively wide range. In general, the process is carried out at temperatures of between 0° C. and 150° C., preferably between 20° C. and 100° C. In general, the reaction time is 2 to 24 hours, preferably 2 to 10 hours.

In general, 1 to 2 moles, preferably 1 to 1.2 moles, of base are employed per 1 mole of hydroxyalkylazole of the formula (II) when carrying out the process according to the invention.

The compounds of the formula (I) are isolated by customary methods. In general, a procedure is followed in which water is added to the reaction mixture, the mixture is then extracted with a sparsely water-miscible organic solvent, and the combined organic phases are concentrated, if appropriate after previously washing them with water. If appropriate, the resulting product can be purified by customary methods, for example by means of chromatography.

Suitable acids for the preparation of acid addition salts of the compounds of the formula (I) are preferably those which have already been mentioned in connection with the description of the acid addition salts according to the invention as being preferred acids.

The acid addition salts of the compounds of the formula (I) can be obtained in a simple manner by customary salt formation methods, for ex ample by dissolving a compound of the formula (I) in a suitable inert solvent and adding the acid, for example hydrochloric acid, and they can be isolated in a known manner, for example by filtering off, and, if required, purified by washing with an inert organic solvent.

Suitable metal salts for the preparation of metal salt complexes of the compounds of the formula (I) are preferably those which have already been mentioned above in connection with the description of the metal salt complexes according to the invention as being preferred metal salts.

The metal salt complexes of compounds of the formula (I) can be obtained in a simple manner by customary methods, such as, for example, by dissolving the metal salt in alcohol, for example ethanol, and adding the mixture to compounds of the formula (I). Metal salt complexes can be isolated in a known manner, for example by filtering off, and, if required, purified by recrystallization.

The active compounds according to the invention exhibit a powerful microbicidal action and can be employed in practice for combating undesired microorganisms. The active compounds are preferably suitable as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries* ; Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

Here, the active compounds according to the invention can be employed particularly successfully for protectively combating Sphaerotheca species in cucumbers and Leptosphaeria species in wheat. In addition, the active compounds according to the invention also have a good fungicidal action against bean rust, apple scab, Pyricularia on rice and also against causative organisms of cereal diseases such as Fusarium, Erysiphe, Puccinia and Cochliobolus.

The active compounds according to the invention moreover engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in a particular desired manner.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also Lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beets, sugar cane, pineapples and citrus fruit or to increase the protein content in soya or cereals, Using growth regulators it is also possible, for example, to inhibit the degradation of desired constituents, such as, for example, sugar in sugar beets or sugar cane, before or after harvesting It is also possible favourably to influence the production or the efflux of secondary plant constituents. The stimulation of latex flux in rubber trees may be mentioned an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tom aloes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds according to the invention are particularly suitable for inhibiting growth of cereals, soy beans, cotton and sugar beets.

The active compounds can be converted to the customary formulations, such as solutions, emulsions, suspensions, powders, foams, pastes, granules, aerosols, very fine capsules in polymeric substances and in coating compositions for seed, as well as ULV formulations, These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-disperse silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolysis products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the substances according to the invention are used as fungicides, the amounts used can be varied within a relatively wide range, depending on the type of application. When parts of plants are treated, the concentrations of active compound in the use forms are thus in general between 1 and 0.0001% by weight, preferably between 0.5 and 0.001%. When seed is treated, amounts of active compound of 0.001 to 50 g per kilogram of seed, preferably 0.01 to 10 g, are generally required. Treatment of the soil requires concentrations of active compound of 0.00001 to 0.1% by weight, preferably 0.0001 to 0.02%, at the site of action.

When the compounds according to the invention are employed as plant growth regulators, the amounts used can be varied within a relatively wide range. In general, 0.01 to 50 kg, preferably 0.05 to 10 kg of active compound are used per hectare of soil surface.

When the substances according to the invention are employed as plant growth regulators, the rule is that the application is carried out within a preferred period of time, the exact definition of which depends on the climatic and vegetative circumstances.

The preparation and the use of the active compounds according to the invention can be seen from the examples below.

PREPARATION EXAMPLES

EXAMPLE 1

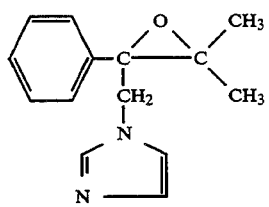

9 g (0.0253 mole) of 3,3-dimethyl-3-(4-chlorophenoxy)-2-phenyl-1-(imidazol-1-yl)-2-propanol are dissolved in 50 ml of dioxane, at room temperature. 0.8 g (0.027 mole) of sodium hydride are added to the mixture, the mixture is stirred for 10 minutes, warmed slowly at reflux temperature and stirred for 10 hours. The reaction mixture is then allowed to cool to room temperature and poured into water, the mixture is extracted with dichloromethane and the organic phase is concentrated under reduced pressure. The residue is chromatographed on silica gel using a mixture of ethyl acetate/cyclohexane=3:1 as the eluent.

4.0 g (69.4% of theory) of 3,3-dimethyl-2-phenyl-2-(imidazol-1-yl-methyl)-oxirane is obtained as an oil [$^1$H NMR*: δ (1.01 (s)3H; 1.65 (s)3H)].

*) The $^1$H-NMR spectra were recorded in deuterochloroform (CDCl$_3$) with tetramethylsilane (TMS) as the internal standard. The chemical shift is indicated as value in ppm.

The compounds of the formula (I) listed in Table 2 below are prepared in analogy to Example 1 and considering the instructions in the process according to the invention:

TABLE 2

| Example No. | R$^1$ | R$^2$ | X | Y$_m$ | Physical constants |
|---|---|---|---|---|---|
| 2 | CH$_3$ | CH$_3$ | N | —⟨C$_6$H$_4$⟩—F | Melting point: 74° C. |
| 3 | CH$_3$ | CH$_3$ | N | —⟨C$_6$H$_4$⟩—Cl | $^1$H-NMR*): δ = 1.60(s)3H; 0.93(s)3H |
| 4 | CH$_3$ | CH$_3$ | N | —⟨C$_6$H$_5$⟩ | $^1$H-NMR*): δ = 1.71(s)3H; 1.05(s)3H |
| 5 | CH$_3$ | CH$_3$ | N | —⟨C$_6$H$_4$⟩ (Cl ortho) | $^1$H-NMR*): δ = 1.59(s)3H; 1.01(s)3H |
| 6 | CH$_3$ | CH$_3$ | N | —⟨C$_6$H$_3$⟩(Cl,Cl) | $^1$H-NMR*): δ = 1.69(s)3H; 1.08(s)3H |
| 7 | CH$_3$ | CH$_3$ | N | —⟨C$_6$H$_4$⟩—Cl | $^1$H-NMR*): δ = 1.70(s)3H; 1.06(s)3H |

*)The $^1$H-NMR spectra were recorded in deuterochloroform (CDCl$_3$) with tetramethylsilane (TMS) as the internal standard. The chemical shift is indicated as value in ppm.

USE EXAMPLES

In the following use examples, the compounds given below are employed as comparison substances:

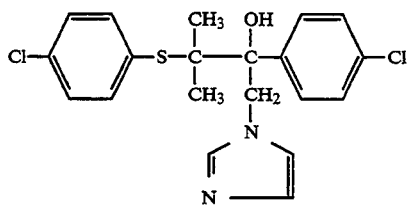
(A)

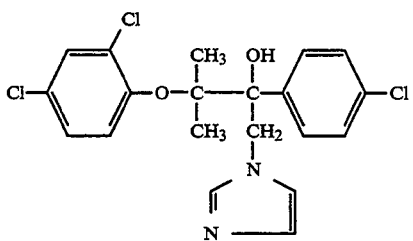
(B)

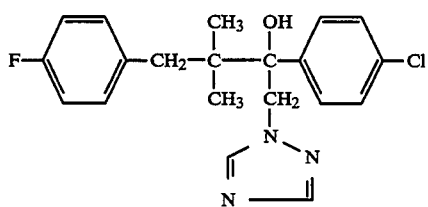
(C)

The compounds (A), (B) and (C) are disclosed in DE-OS (German Published Specification) 3,245,504.

EXAMPLE A

*Sphaerotheca* test (cucumber)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a considerably better activity than comparison substances (A) and (B) is shown by the compounds according to the invention listed in Examples (3), (5) and (7).

EXAMPLE B

*Leptosphaeria nodorum* test (wheat)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabin at 20° C. and 100% relative atmospheric humidity.

The plants are placed in a greenhouse at a temperature of about 15° C. and a relative atmospheric humidity of about 80%.

In this test, a considerably better activity than comparison substance (C) is shown by the compounds according to the invention listed in Examples (1) and (4).

EXAMPLE C

Growth of soy beans

Solvent: 30 parts by weight of dimethylformamide

Emulsifier: 1 part by weight of polyoxyethylene sorbitan monolaurate

To produce a suitable preparation of active compound, 1 part by weight of active compound is mixed with the stated amounts of solvent and emulsifier and the mixture is made up to the desired concentration with water.

Soya bean plants are grown in a greenhouse until the first secondary leaf has unfolded completely. In this stage, the plants are sprayed with the preparations of active compound until dripping wet. After 2 weeks, the additional growth is measured on all the plants and the growth in percent of the additional growth of the control plants is calculated. 100% growth denotes a growth corresponding to that of the control plants and 0% means that growth has stopped. Values over 100% denote promotion of growth.

In this test, the active compound (3) according to the invention shows a powerful inhibition of growth.

EXAMPLE D

Growth of cotton

Solvent: 30 parts by weight of dimethylformamide

Emulsifier: 1 part by weight of polyoxyethylene sorbitan monolaurate

To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 2 weeks, the additional growth of the plants is measured and the inhibition of growth in per cent of the growth of the control plants is calculated. 100% growth means a growth corresponding to that of the control plants and 0% means that growth has stopped. Values over 100% denote promotion of growth.

In this test, the active compound (3) according to the invention shows a powerful inhibition of growth.

EXAMPLE E

Growth of sugar beets

Solvent: 30 parts by weight of dimethylformamide

Emulsifier: 1 part by weight of polyoxyethylene sorbitan monolaurate

To produce a suitable preparation of active compound, 1 part by weight of active compound is mixed with the stated amounts of solvent and emulsifier and the mixture is made up to the desired concentration with water.

Sugar beet is grown in a greenhouse until formation of the cotyledons is complete. In this stage, the plants are sprayed with the preparations of active compound until dripping wet. After 14 days, the additional growth of the plants is measured and the growth in percent of the additional growth of the control plants is calculated. 100% growth denotes a growth which corresponds to that of the control plants and 0% growth means that growth has stopped. Values over 100% denote promotion of growth.

In this test, the active compound (3) according to the invention shows a powerful inhibition of growth.

It will be appreciated that the instant specification and claims are set forth by way of illustration and not limitation, and that various modifications and changes may be made without departing from the spirit and scope of the present invention.

What is claimed is:

1. A substituted triazolylmethyloxirane of the formula

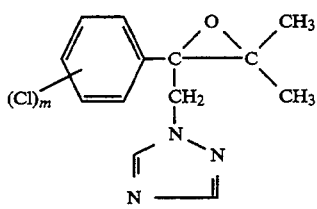

wherein m is 0 or 1 or an addition product thereof with an acid or metal salt.

2. A compound according to claim 1, wherein such compound is 3,3-dimethyl-2-(4-chloro-phenyl)-2-(1,2,4-triazol-1-yl-methyl)-oxirane of the formula

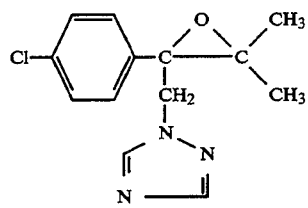

or an addition product thereof with an acid or metal salt.

3. A compound according to claim 1, wherein such compound is 3,3-dimethyl-2-phenyl-2-(1,2,4-triazol-1-yl-methyl-oxirane of the formula

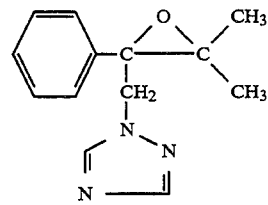

or an addition product thereof with an acid or metal salt.

4. A compound according to claim 1, wherein such compound is 3,3-dimethyl-2-(2-chloro-phenyl)-2-(1,2,4-triazol-1-yl-methyl)-oxirane of the formula

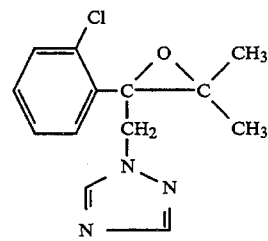

or an addition product thereof with an acid or metal salt.

5. A compound according to claim 1, wherein such compound is 3,3-dimethyl-2-(3-chloro-phenyl)-2-(1,2,4-triazol-1-yl-methyl)-oxirane of the formula

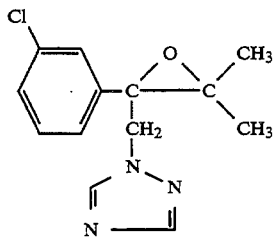

or an addition product thereof with an acid or metal salt.

6. A fungicidal composition comprising a fungicidally effective amount of a compound or addition product thereof according to claim 1 and an inert diluent.

7. A method of combating fungi which comprises applying to such fungi or to a fungus habitat a fungicidally effective amount of a compound or addition product thereof according to claim 1.

8. The method according to claim 7, wherein such compound is
3,3-dimethyl-2-(4-chloro-phenyl)-2-(1,2,4-triazol-1-yl-methyl)-oxirane,
3,3-dimethyl-2-phenyl-2-(1,2,4-triazol-1-yl-methyl)-oxirane,
3,3-dimethyl-2-(2-chloro-phenyl)-2-(1,2,4-triazol-1-yl-methyl)-oxirane, or
3,3-dimethyl-2-(3-chloro-phenyl)-2-(1,2,4-triazol-1-yl-methyl)-oxirane,
or an addition product thereof with an acid or metal salt.

9. A plant growth-regulating composition comprising a plant-growth-regulating effective amount of a compound or addition product thereof according to claim 1 and an inert diluent.

10. A method of regulating the growth of a plant which comprises applying to such plant or to a locus in which such plant is growing or is to be grown a plant growth-regulating effective amount of a compound or addition product thereof according to claim 1.

11. The method according to claim 10, wherein such compound is 3,3-dimethyl-2-(4-chloro-phenyl)-2-(1,2,4-triazol-1-yl-methyl)-oxirane 3,3-dimethyl-2-phenyl-2-(1,2,4-triazol-1-yl-methyl)-oxirane, 3,3,-dimethyl-2-(2-chloro-phenyl)-2-(1,2,4-triazol-1-yl-methyl)-oxirane, or 3,3-dimethyl-2-(3-chloro-phenyl) -2-(1,2,4-triazol-1-yl-methyl)-oxirane, or an addition product thereof with an acid or metal salt.

* * * * *